United States Patent [19]
Graettinger et al.

[11] Patent Number: 5,839,438
[45] Date of Patent: Nov. 24, 1998

[54] COMPUTER-BASED NEURAL NETWORK SYSTEM AND METHOD FOR MEDICAL DIAGNOSIS AND INTERPRETATION

[75] Inventors: Timothy Joseph Graettinger, Bethel Park, Pa.; Paul Alton DuBose, Hillsborough, N.C.

[73] Assignee: Neuralmed, Inc., Durham, N.C.

[21] Appl. No.: 712,986

[22] Filed: Sep. 10, 1996

[51] Int. Cl.$^6$ .................................................. A61B 19/00
[52] U.S. Cl. ......................... 128/630; 128/904; 128/924
[58] Field of Search ................................. 128/630, 904, 128/924

[56] References Cited

U.S. PATENT DOCUMENTS

| | | | |
|---|---|---|---|
| 5,455,890 | 10/1995 | Wang | 395/22 |
| 5,463,548 | 10/1995 | Asada et al. | 364/413.02 |
| 5,486,999 | 1/1996 | Mebane | 364/401 |
| 5,491,627 | 2/1996 | Zhang et al. | 364/413.2 |

OTHER PUBLICATIONS

Zurada et al., Sensitivity Analysis for Minimization of Input Data Dimension for Feedforward Neural Network, 1994 IEEE International Symposium on Circuits and Systems, vol. 6, pp. 447–450.

Srivastava, Rajeshwar Prasad, Automating Judgmental Decisions Using Neural Newworks: A Model for Processing Business Loan Applications; Proceedings of SCS 92: ACM 20th Annual Computer Science Conference, Kansas City, MO, Mar. 3–5, 1992, pp. 351–357.

Yeung et al., Knowledge Matrix—An Explanation & Knowledge Refinement Facility for a Rule Induced Neural Network, Proceedings of the 12th National Conference on Aritficial Intelligence, vol. 2, pp. 889–894.

Pau et al., Explanation Facility for Neural Networks; Journal of Intelligent and Robotic Systems 5: 193–206, 1992.

Angell et al., Faster Than a Speeding Neural Network; Software Review, Al Expert, Nov. 1992, pp. 50–53.

Kim et al., A Neural Network Capable of Learning and Inference for Visual Pattern Recognition; Pattern Recognition, vol. 27, No. 10, pp. 1291–1302, 1994.

Kim et al., A Fuzzy Connectionist Expert System for Visual Pattern Classification; Robotics & Computer–Integrated Manufacturing, vol. 11. No. 3, pp. 233–244, 1994.

Yoon et al., Integrating Artificial Neural Networks With Rule–Based Expert Systems; Decision Support Systems II (1994) pp. 497–507.

*Primary Examiner*—William E. Kamm
*Attorney, Agent, or Firm*—Pennie & Edmonds LLP

[57] ABSTRACT

A neural network system and method for diagnosing patients' medical conditions provide an efficient aid in identifying and interpreting factors which are significant in the medical diagnosis. The neural network is trained to recognize medical conditions by being provided with input data that is available for a number of patients, and diagnosis made by physicians in each case. Upon completion of the training period the neural network system uses input measurement and interview data to produce a score, or a graded classification, of a patient's medical condition that is accompanied with a diagnosis interpretation. The interpretation is a sorted catalogue of individual factors and interactions that influenced the score. The interpretive facility of the present invention is based on comparison with a set of nominal values for each input factor or interaction. It can assist the physician in making a diagnosis of the patient's condition and can further provide a "second opinion" that may confirm the physician's findings or point to ambiguities that call for a more detailed analysis.

29 Claims, 10 Drawing Sheets

COMPUTER-BASED NEURAL NETWORK SYSTEM AND METHOD FOR MEDICAL DIAGNOSIS AND INTERPRETATION

FIELD OF THE INVENTION

The present invention relates to medical diagnosis and more specifically to a system and method using neural networks for the diagnosis and interpretation of medical conditions.

BACKGROUND OF THE INVENTION

The medical diagnosis task can be decomposed into three basic steps as follows: 1. detection; 2. classification; and 3. recommendation. Detection refers to the step in which symptoms associated with one or more specific illnesses or conditions are first recognized. Classification is the process of designating or naming the condition, for instance, categorizing the condition into a known diagnostic group. Finally, recommendation is the step in which the physician prescribes a course of treatment for the condition.

The following problems are often encountered when performing one or more of these diagnosis steps in a typical, clinical setting.

Consistency—On any given day, a physician may be fatigued or under stress. She or he may be inexperienced in a particular medical specialty. Identical clinical data and parameter values monitored for one patient may be interpreted differently by two physicians, due to their different medical training, experience level, stress level, or other factors.

Transference/Interpretation—One physician's mental rules in the diagnosis of a medical condition may be hard to describe, and hence, difficult to transfer from one physician to another. These mental rules may also be difficult to explain to a patient if he asks how the physician arrived at the diagnosis, or even to document reasoning for use by other physicians.

Nonlinearity—When the relationships between the monitored values and the patient's condition are complex and not well-understood, conventional (e.g., linear, statistical) models are often inaccurate and thus not sufficient or reliable. Therefore, diagnostic technology using more complex nonlinear models is clearly preferable and often necessary.

These and other problems which are related at least in part to human errors and limitations in the area of medical diagnosis can be addressed successfully using computer-aided diagnostic tools. Conventional computer-aided medical diagnosis is based on statistical data analysis. More advanced diagnostic tools are based on artificial intelligence (AI) technology which generally involves expert systems, fuzzy logic, artificial neural networks and various combinations thereof. The advent of effective commercially available software and hardware tools of these types has greatly broadened the base of potential and realized medical applications. More recent examples of such use are disclosed in U.S. Pat. Nos. 5,491,627, 5,486,999, 5,463,548 and 5,455,890. Still, none of the presently available medical diagnostic tools is capable of adequately addressing the problems discussed above.

Deficiencies in the Related Art

Conventional computer-aided data processing techniques, such as linear regression, are difficult to implement successfully without well-defined relationships between the monitored values (inputs) and the patient condition (output). However, such well-defined relationships are seldom available especially because many medical conditions share common symptoms and are therefore difficult to detect and classify.

Expert systems represent a different AI approach in which complex systems are modeled using a set of Production Rules (i.e., IF/THEN rules). Expert systems are popular because of their design simplicity, and their capability to recommend actions by inference or search. They have been shown to be beneficial in diagnosis problems under certain circumstances. However, the rule based approach used in these systems requires a complete understanding of the task to be automated before an expert system can be implemented. Moreover, the large number of Production Rules required for increased robustness in the modeling of complex systems often slows down the decision making process and aggravates maintenance due to the sheer number of rules to be kept track of.

Fuzzy logic is typically used in situations where data and functional relationships cannot be expressed in clear mathematical terms. Instead, "fuzzy" relational equations are applied in which quantifiers such as "for many" of "for a few" are used to relate elements of different sets. Fuzzy logic systems provide conceptual advantages, but require both intuition and experience in the proper design of working medical diagnosis systems.

Artificial neural networks ("neural networks") are networks of neuron-like units that can modify themselves by adapting to changing conditions. Unlike traditional AI systems which are rule based, neural networks are very flexible and provide the capability of simulating complex nonlinear systems the behavior of which is not well understood. This makes them uniquely suitable for medical diagnosis applications. Generally, neural networks mimic the ability of the human brain to recognize recurring patterns on the basis of an inventory of previously learned patterns. In particular, they can predict the value of an output variable based on input from several other input variables that can impact it. The prediction is made by selecting from a set of known patterns the one that appears most relevant in a particular situation. Because of their flexibility in modeling complex systems, neural nets have been widely used in the medical practice.

Still, prior art neural networks address the diagnosis problem as a black box solution: given a set of input parameters they generate a score, i.e., an estimate of the likelihood of the patient's condition, but lack any interpretive facility. In particular, they provide no further information to assist the physician in positively affecting the patient's condition. Notably missing in prior art systems is the capability to identify factors which were critical in the diagnosis of the patient's medical condition. Accordingly, such systems provide little basis for consensus with the physician's opinion and findings when only a single score, without further explanation, is provided.

Thus, it can be seen that prior art diagnostic tools based on classical statistical methods, expert system methods, and simple neural network methods have significant limitations when applied to medical diagnosis problems especially where a disease or a medical condition can be diagnosed, but the diagnosis is not well-understood. Therefore, there is a need to develop a computer-aided medical diagnosis system and method that are capable of not only determining the nature and the likelihood of a particular medical condition, but also of providing an interpretation that identifies and catalogues all factors that were significant in the process of making the determination.

SUMMARY OF THE INVENTION

Accordingly, it is an object of the present invention to provide a data processing system for medical diagnosis and interpretation of medical conditions.

It is another object of the present invention to present a neural network system for estimating the likelihood of a medical condition on the basis of measurement, interview data and other input factors, and for interpreting the diagnostic output using analysis of the contribution of various input factors.

It is yet another object of the present invention to develop a system and method for presenting in human-readable form an interpretation of a variety of input factors taken into account in the process of modeling complex medical conditions using neural networks.

These and other objects are achieved in accordance with the present invention by providing a novel medical diagnosis system including a neural network. More specifically, the present invention is a neural network system and method for diagnosing and interpreting a patient's medical condition. The neural network is trained by being provided with the diagnosis made by a physician and with the measurement and interview data that was available to the physician. In case-by-case operation, the neural network system uses measurement and interview data to produce a score, or graded classification, of the patient's medical condition. In the present invention, this score is accompanied with an interpretation that is a sorted list of individual factors and interactions that influenced the score. The trained network and the interpretation can be used to assist the physician in the diagnosis of the patient's condition. Thus, the system and method of the present invention provide a "second opinion" that can confirm the physician's findings or point to ambiguities that call for more detailed analysis. Lacking the interpretive facility of the present invention, a neural network is simply a "black box" that provides no window into the patient's condition. This window is critical to patient and physician acceptance of this powerful, nonlinear diagnostic tool.

More specifically, in a preferred embodiment, the method for diagnosis of a medical condition of the present invention comprises the steps of: providing a plurality of input parameters representing characteristics of the medical condition; converting the plurality of input parameters into numerical data; inputting the numerical data to a neural network trained to detect the medical condition and determining a score indicative of the likelihood of the medical condition on the basis of the numerical data; interpreting the numerical data to provide estimates of the contribution of input parameters to the determined score; and displaying the determined score and the provided estimates in a human-readable form.

In a preferred embodiment, the system for diagnosis and interpretation of a medical condition of the present invention comprises: means for providing a plurality of input parameters representing characteristics of the medical condition, the plurality of input parameters being provided as numerical data; a neural network trained to detect the medical condition for determining a score indicative of the likelihood of the medical condition on the basis of the numerical data; means for interpreting the numerical data to provide estimates of the contribution of input parameters to the determined score; and display means for displaying the determined score and the provided estimates in a human-readable form.

Another aspect of the present invention is a computer-based system to assist the diagnosis of a medical condition, comprising: a patient record representing in numerical form a plurality of input factors associated with characteristics of the medical condition; a neural network responsive to said patient record and configured to determine a score indicative of the likelihood of the medical condition in the patient record; a computer interpreter responsive to said patient record for estimating the contribution of input factors to the score determined in the neural network; and a display for displaying the determined score and the estimates provided by the interpreter in a human-readable form to assist the diagnosis of the medical condition.

BRIEF DESCRIPTION OF THE DRAWINGS

The present invention, as defined by the claims, is better understood with reference to the following detailed description of the preferred embodiments read in conjunction with the accompanying drawings, in which:

DETAILED DESCRIPTION OF THE PREFERRED EMBODIMENTS

In the following description like numbers designate like elements or processing steps, as illustrated in the accompanying figures.

Figure 10:
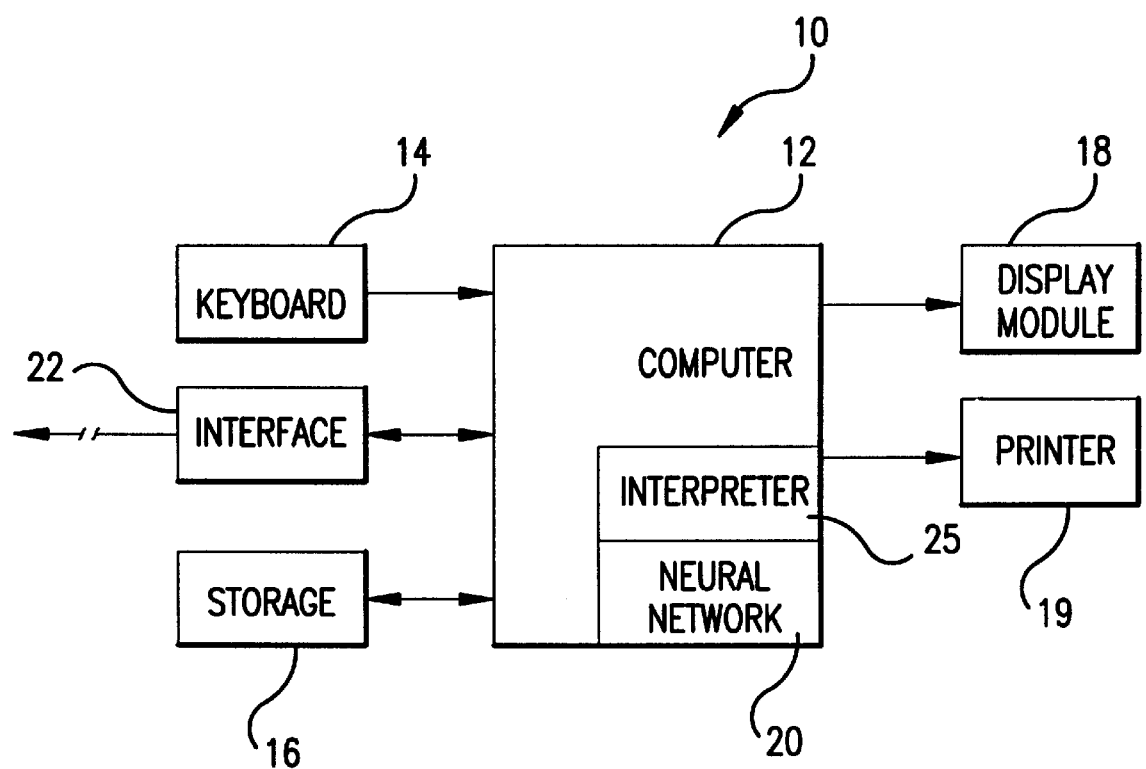
FIG. 10 is a block diagram of one embodiment of the data processing system for use in the present invention.

FIG. 10 illustrates a processing system 10 for use in the present invention. Processing system 10 generally comprises a computer 12 which is adapted to receive input data from an operator by means of a keyboard 14 or from other sources, such a patient database stored in memory 16. Memory 16 can also be used to store output data from the computer 12. Computer 12 is also coupled to display module 18 which may be a computer monitor or similar device. The system further comprises a printer 19 for providing a hard copy of the diagnostic results. In a preferred embodiment of the present invention system 10 further comprises interface 22, such as a modem, for connection to a network of computers.

Computer 12 of the system is a conventional computer that executes a simulation of a neural network 20 and an interpreter unit 25. Typical computers that can be used in accordance with the present invention include general purpose desktop computers, such as an IBM computers, a Hewlett-Packard computers or Sun workstations. Computer 12 may also be a mainframe computer, a server or a workstation. In a preferred embodiment of the system 10 of the present invention, a Silicon Graphics Indigo 2 system was used with MIPS R4400 250 MHz CPU, MIPS R4010 FPU, 64 MB of RAM, GR3 Elan Graphics Board, A2 Audio Processor, 2020 MB SCSI Disk, Floptical Disk and a CDROM Drive. The system in the preferred embodiment uses an IRIX 5.3 (Silicon Graphics) Operating System.

In a specific embodiment of the present invention computer 12 is connected via interface 22 to a Local Area Network (LAN), Wide Area Network (WAN) or a packet switched network, such as the Internet. Accordingly, the information generated by processing system 10 can be accessible from any computer on the LAN or WAN or the Internet, as the case may be, and can be assimilated by existing database management software. In addition, processing system 10 may include various other input/output (I/O) and peripheral modules, as known in the art.

In a preferred embodiment of the present invention, neural network 20 and interpreter unit 25 are software simulations of a collection of processing elements. Alternatively, the neural network may be simulated using commercially available software packages such as the BrainMaker Professional, marketed by California Scientific Software, NeuralWorks Professional from NeuralWare Inc., Neuroshell 2, distributed by the Ward Systems Group, and others. On the basis of the present disclosure, a person skilled in the art will also be able to use other neural network software or hardware. Both units 20 and 25 are considered in more detail next.

Overview of Neural Networks

To fully appreciate the various aspects and benefits produced by the present invention, a basic understanding of neural network technology is required. Following is a brief discussion of this technology, as applicable to the medical diagnosis system and method of the present invention.

Figure 1:
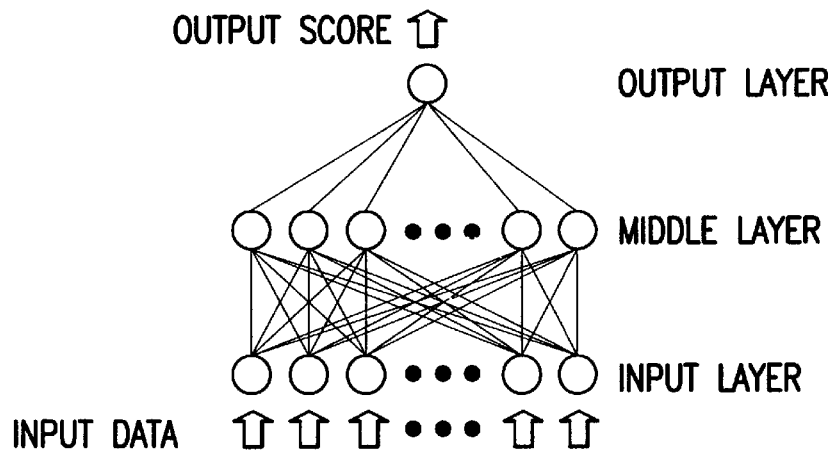
FIG. 1 is a schematic diagram of a neural network having an input layer of processing elements, a middle layer of processing elements, and an output layer composed of a single processing element.

Artificial neural networks loosely model the functioning of a biological neural network, such as the human brain. Accordingly, neural networks are typically implemented as computer simulations of a system of interconnected neurons. In particular, neural networks are hierarchical collections of interconnected processing elements configured, for example, as shown in FIG. 1. Specifically, FIG. 1 is a schematic diagram of a standard neural network having an input layer of processing elements, a middle layer of processing elements, and an output layer composed of a single processing element. The example shown in FIG. 1 is merely an illustrative embodiment of a neural network 20 that can be used in accordance with the present invention. Other embodiments of a neural network can also be used, as discussed next.

Turning next to the structure of a neural network, each of its processing elements receives multiple input signals, or data values, that are processed to compute a single output. The output value is calculated using a mathematical equation, known in the art as an activation function or a transfer function that specifies the relationship between input data values. As known in the art, the activation function may include a threshold, or a bias element. As shown in FIG. 1, the outputs of elements at lower network levels are provided as inputs to elements at higher levels. The highest level element produces a final system output.

In the context of the present invention, neural network 20 is a computer simulation that produces a score, or graded classification, of a patient's medical condition, based on available measurements, interview responses and other input factors. For instance, the scores produced by the network might range continuously from zero to one, with scores near zero indicating a low likelihood of disease and scores near one indicating a high likelihood of disease.

A. Construction of Neural Networks

With reference to FIGS. 1 and 10, the neural network 20 in the present invention is constructed by specifying the number, arrangement, and connection of the processing elements which make up the network. A simple embodiment of a neural network consists of a fully connected network of processing elements. As shown in FIG. 1, the processing elements are grouped into layers: an input layer where data on the patient's condition are introduced; a middle layer of processing; and an output layer where the resulting patient score is produced. The number of connections, and consequently the number of connection weights, is fixed by the number of elements in each layer.

In a preferred embodiment of the present invention, the data types provided at the input layer remain constant. In addition, the same mathematical equation, or transfer function, is normally used by the elements at the middle and output layers. The number of elements in each layer is generally dependent on the particular application. As known in the art, the number of elements in each layer in turn determines the number of weights and the total storage needed to construct and apply the network. Clearly, more complex networks generally require more configuration information and therefore more storage.

In addition to the structure illustrated in FIG. 1, the present invention contemplates other types of neural network configurations for the neural network module 20. All that is required by the present invention is that a network 20 be able to be trained and retrained, if necessary, to produce the scores utilized in the patient's diagnostic assessment.

B. Scoring

Referring back to FIG. 1, the operation of a specific embodiment of a feedforward neural network is described in more detail next. It should be noted that the following description is only illustrative of the way in which a neural network 20 used in the present invention can function.

Specifically, in operation input data is provided to the input layer of processing elements, referred to hereafter as inputs. As shown in FIG. 1, the middle layer elements are connected by links to the inputs, each link having an associated connection weight. The output values of the input processing elements propagate along these links to the middle layer elements. Each element in the middle layer multiplies the input value along the link by the associated weight and sums these products over all of its inks. The sum for an individual middle layer element is then modified according to the activation function of the element to produce the output value for that element. In accordance with the different embodiments of the present invention the processing of the middle layer elements can occur serially or in parallel.

If only one middle layer is present, as shown in a specific embodiment of the present invention in FIG. 1, the last step in the operation of the neural network is to compute the output, or the patient's score by the output layer element. To this end, the output values from each of the middle layer processing elements are propagated along their links to the output layer element. Here, they are multiplied by the associated weight for the link and the products are summed over all links. The computed sum is finally modified by the transfer function equation of the output processing element. The result is the final output or score which, in accordance with a preferred embodiment of the present invention, is a grade of the patient's condition.

In a preferred embodiment of the present invention, input data provided to the layer of input processing elements for the scoring of a medical condition can vary dependent on the particular condition. A number of different input data types can be used to this end. For example, this can include clinical information such as the patient's age, sex, the duration and severity of symptoms, his or her temperature, immune status and others. Input data may also reflect a variety of radiographic or ultrasound findings, digital images representing sections of the patient's body and others. It is important to note that the selection of particular input factors is dependent on the medical condition and may vary without deviating from the general principles of the present invention.

As with most empirical modeling technologies, neural network development requires a collection of data properly formatted for use. Specifically, as known in the art, input data and/or the outputs of intermediate network processing layers may have to be normalized prior to use. One conventional approach which can also be used in the present invention is to create an appropriate disk file on the computer on which the neural network is configured and run. Data normalization and other formatting procedures used in accordance with the present invention are known to those skilled in the art and will not be discussed in any further detail.

Example 1 attached hereto provides further insight into the selection and use of the input factors in a specific application of the system and method of the present invention.

C. Training

With reference to FIG. 10, in accordance with a preferred embodiment of the present invention the neural network 20 is trained by being provided with the diagnosis made by a physician and with input data, such as measurement and interview data that was available to the physician. In the sequel, the diagnosis along with the corresponding input measurement and interview data is referred to as a data record. All available data records, possibly taken for a number of different patients, comprise a data set. In accordance with the present invention, a data set corresponding to a particular medical condition is stored in memory 16 and is made available for use by the processing system 10 for training and diagnostic measurements.

A typical training mechanism used in a preferred embodiment of the present invention is briefly described next. Generally, as stated above, the specifics of the training process are largely irrelevant for the operation of the diagnostic processing system 10. In fact, all that is required is that the neural network 20 be able to be trained and retrained, if necessary, to produce acceptably accurate scores for patient assessment. As known in the art, a myriad of techniques has been proposed in the past for training feed-forward neural networks. Most currently used techniques are variations of the well-known error backpropagation method. The specifics of the method need not be considered in detail here. For further reference and more detail the reader is directed to the excellent discussion provided by Rumelhardt et al. in "Parallel Distributed Processing: Explorations in the Microstructure of Cognition," vol. 1 and 2, Cambridge: MIT Press (1986), and "Explorations in Parallel Distributed Processing, A Handbook of Models, Programs, and Exercises," which are incorporated herein by reference.

Briefly, in its most common form backpropagation learning is performed in three steps:
1. Forward pass
2. Error backpropagation
3. Weight adjustment As to the forward pass step, in accordance with the present invention a single data record is provided to the input layer of the network. This input data propagates forward along the links to the middle layer elements which compute the weighted sums and transfer functions, as described above. Likewise, the outputs from the middle layer elements are propagated along the links to the output layer element. The output layer element computes the weighted sum and transfer function equation to produce the patient score.

In the following step of the training process, the physician diagnosis associated with the data record is made available. At that step, the score produced by the neural network is compared with the physician's diagnosis, which is expressed in mathematically comparable terms as a numerical score. Next, an error signal is computed as the difference between the score corresponding to the physician's diagnosis and the neural network score. This error is propagated from the output element back to the processing elements at the middle layer through a series of mathematical equations, as known in the art. Thus, any error in the neural network score is partially assigned to the processing elements that combined to produce it.

As described earlier, the outputs produced by the processing elements at the middle layer and the output layer are mathematical functions of their connection weights. Errors in the outputs of these processing elements are attributable to errors in the current values of the connection weights. Using the errors assigned at the previous step, weight adjustments are made in the last step of the backpropagation learning method according to mathematical equations to reduce or eliminate the error in the neural network score.

The steps of the forward pass, error backpropagation, and weight adjustment are performed repeatedly over the records in the data set. Through such repetition, the training of the neural network 20 is completed when the connection weights stabilize to certain values that minimize, at least locally, the diagnosis errors over the entire data set.

In addition to backpropagation training, weight adjustments can be made in alternate embodiments of the present invention using different training mechanisms. For example, as known in the art, the weight adjustments may be accumulated and applied after all training records have been presented to the neural network. It should be emphasized, however, that the present invention does not rely on a particular training mechanism. Rather, the only requirement is that the resulting network produce acceptable error rates in its scoring of patient conditions. Naturally, what is an acceptable error rate may in turn depend on the medical condition and other factors which are not considered in this application.

Diagnostic Scoring and Interpretation

Figure 3:
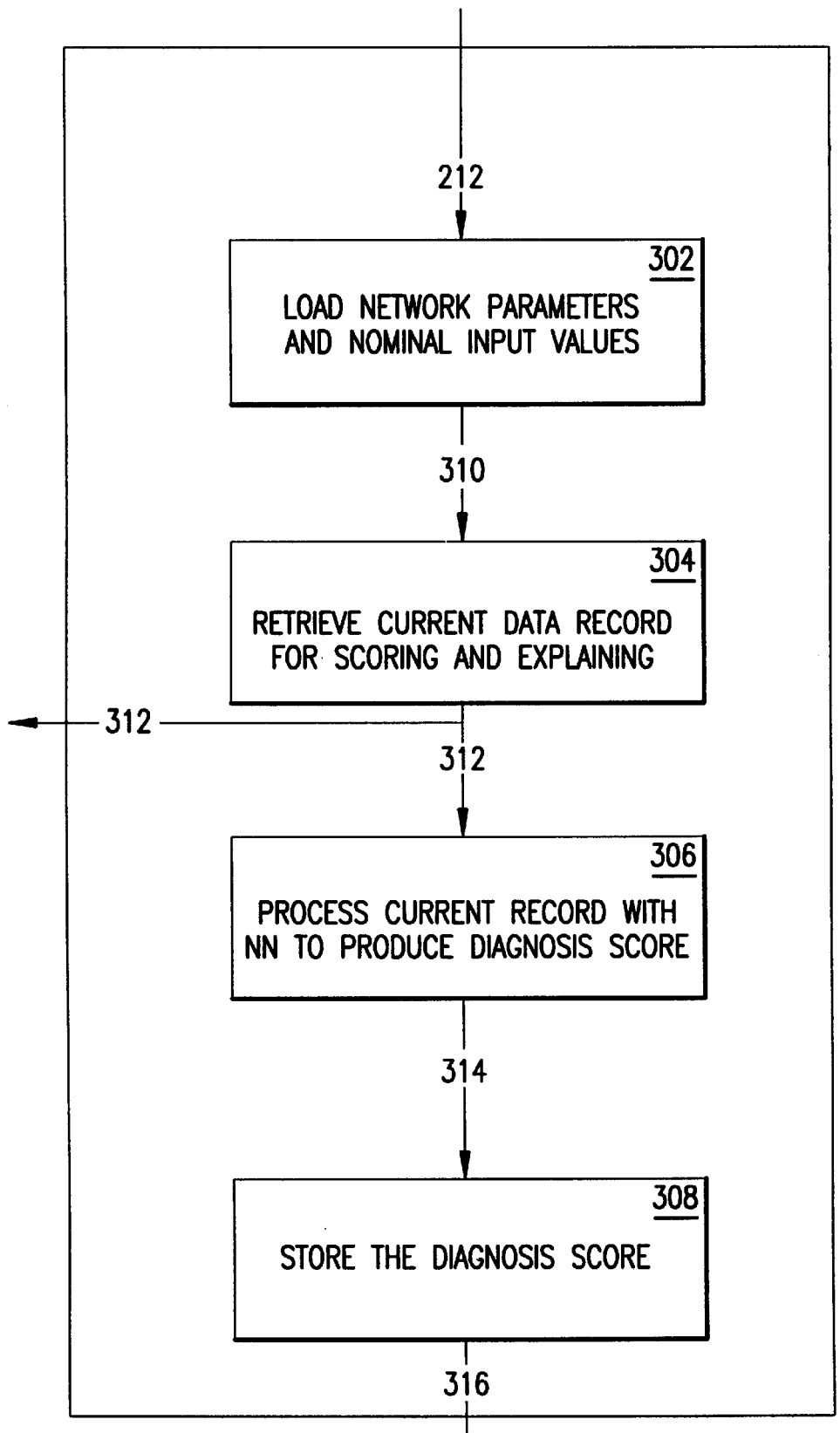
FIG. 3 displays the steps in processing a data record to produce a diagnosis score of the patient's condition.
Figure 4:
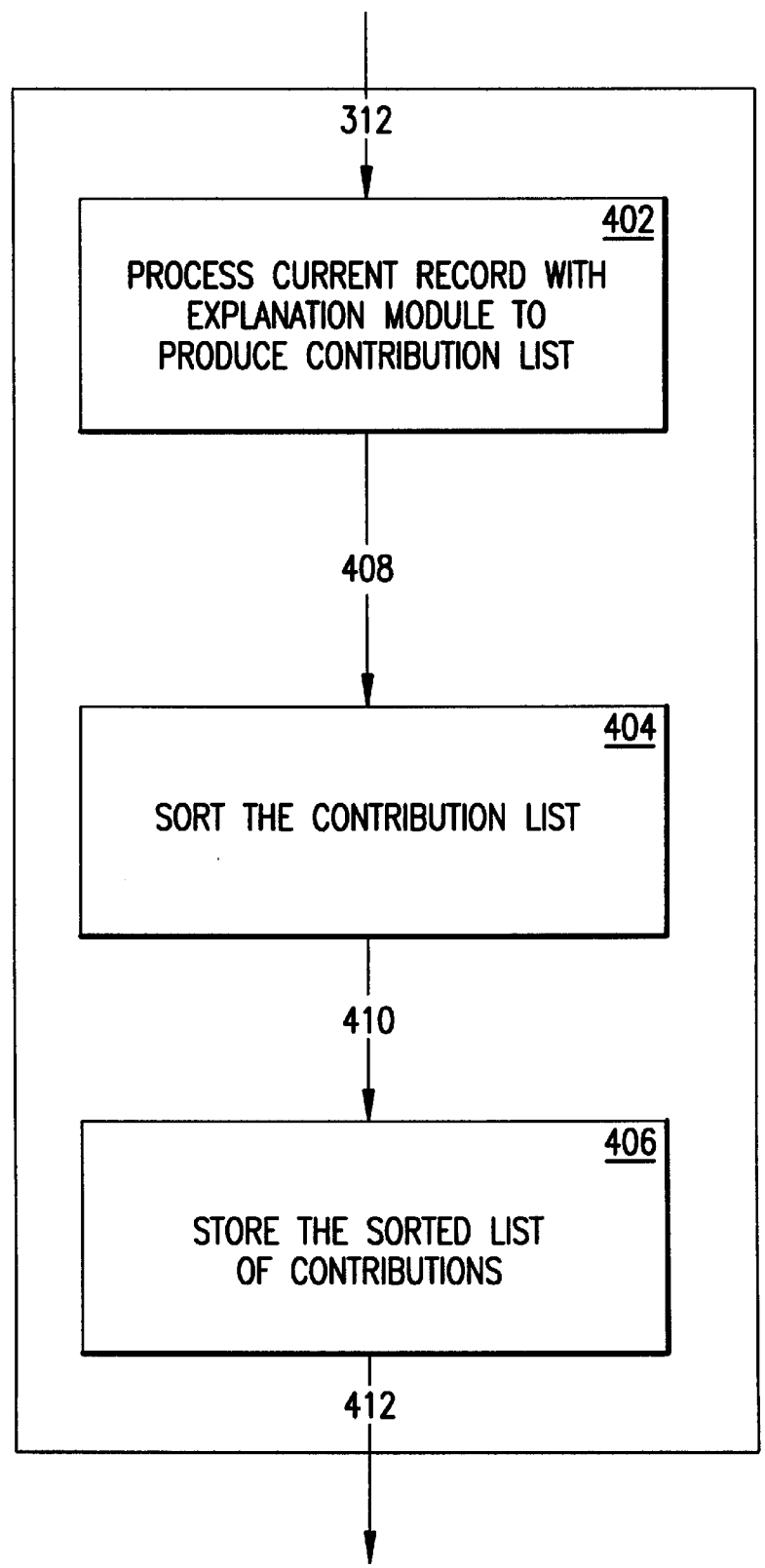
FIG. 4 is a high level block diagram illustrating the interpretation of the diagnosis score produced by the neural network in accordance with the present invention.
Figure 5:
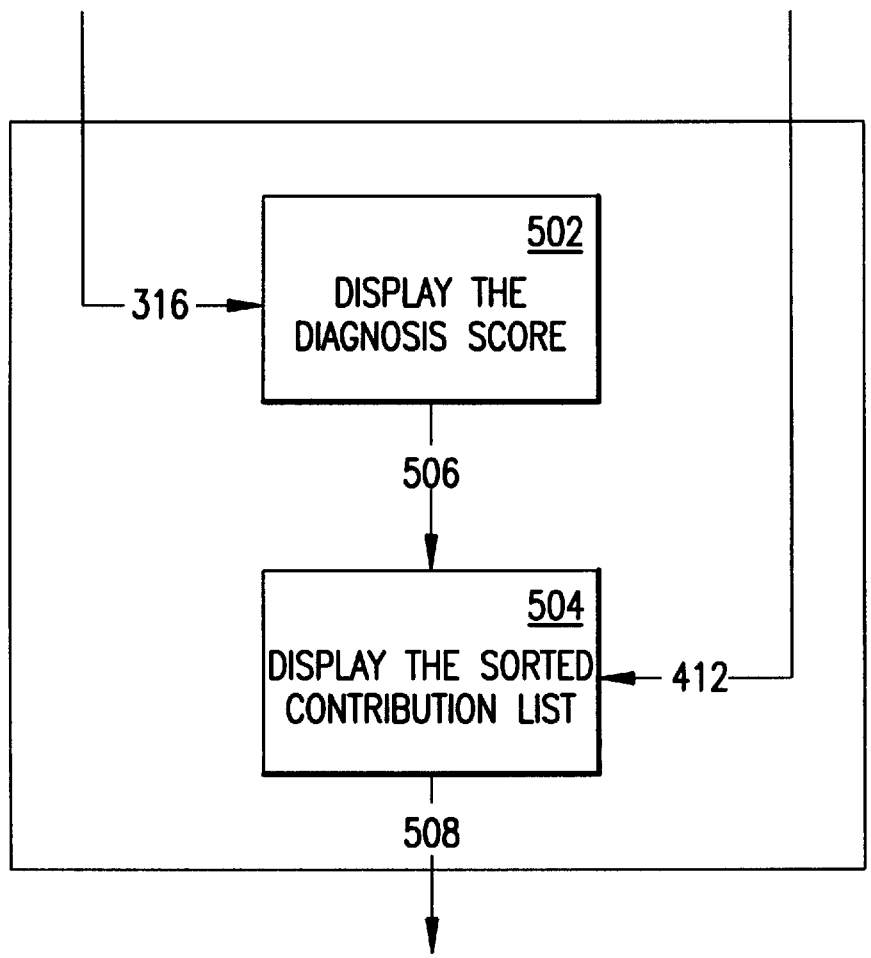
FIG. 5 illustrates the process of collecting diagnostic results and displaying them to a user.

FIGS. 3, 4 and 5 provide a high level description of the proposed novel medical diagnosis system and method having enhanced interpretive facility in accordance with a preferred embodiment of the present invention. Specifically, FIG. 3 illustrates the operation of computer neural network 20 that processes the patient's data record to produce a diagnostic score 316. FIG. 4 is a high level block diagram illustrating the interpretation of the diagnostic score by interpreter unit 25 which, in a preferred embodiment of the proposed system and method, generates an accompanying sorted list of contributions 412 explaining that score. Finally, FIG. 5 illustrates the process of collecting diagnostic results, their interpretation and display to the user.

The operation of the system in a preferred embodiment of the present invention in described in more detail in the following sections. Generally, as shown in FIG. 3, a trained neural network 20 processes in step 306 of the method the input patient record 312 that comprises measured and interview data regarding the patient's condition. A medical diagnostic score which is indicative of the likelihood of a given medical condition in the data record of the patient is computed by the neural network 20 in step 306, it is next stored in step 308, and displayed to the physician in step 502 of the method, as shown in FIG. 5. The diagnostic score produced by the neural network 20 is designed to assist the physician in providing a diagnosis.

The operation of interpreter unit 25 of the present invention is shown in more detail in FIG. 4, in which at step 402 the patient record 312 is processed to produce a catalogue of contributions 408 to the diagnostic score 316. In accordance with a preferred embodiment, the catalogue is a list of contributions of individual input factors obtained as described next. As shown in FIG. 4, the computed list of contributions is sorted in step 404 and stored in step 406 of the method of the present invention. In addition, as shown in FIG. 5 the sorted list is also displayed in step 504 to the physician on the display 18 of the system. In accordance with the present invention the sorted contribution list can be used to confirm the physician's findings or point to important measurements that call for more detailed analysis of the patient's record, when there are differences. In this way, the interpreter unit 25 of the system 10 serves as an adjunct to the physician, providing a "second opinion" in the diagnosis process.

The Method of Operation

The preferred method of operation of the present invention comprises the steps of retrieving input data, computing a diagnostic score, preparing a sorted list of contributions to the score, and displaying the results to a physician. As shown in FIG. 3, several steps are carried out in parallel in the method of the present invention. In particular, as indicated by the divergent order pointer 312, following the loading of network parameters and nominal input values 302 and retrieval of the current data record 304, the steps of scoring and interpreting the score can be carried out in parallel. To this end, in step 306 of the method, input data is processed first by the trained neural network to produce a diagnostic score which is then stored in step 308. Parallel with this, in method step 402 shown in FIG. 4, the explanation facility of interpreter unit 25 is applied to the current data record to generate a contribution list. In the following step 404 of the method, the contribution list is sorted and then stored in step 406. Next, as shown in FIG. 5, in step 502 of the method, the stored diagnostic score is retrieved and displayed. Finally, the sorted contribution list is also retrieved and displayed in step 504.

Figure 2:
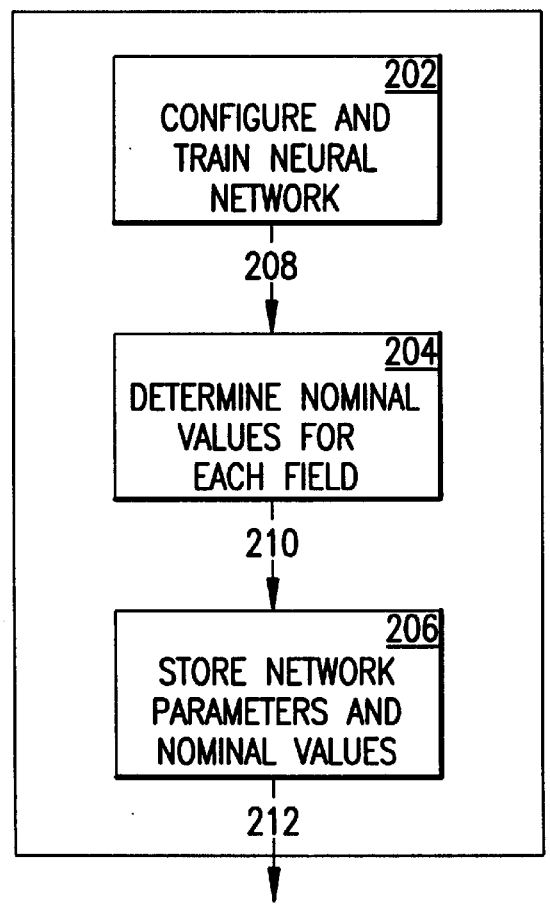
FIG. 2 illustrates the steps in configuring and training a neural network for a diagnosis problem in accordance with a preferred embodiment of the present invention.

Referring back to FIG. 3, network parameters and nominal input values are loaded by the system in step 302. The prerequisite steps to produce the network parameters and nominal input values are illustrated in FIG. 2. Specifically, using standard techniques, a designer of ordinary skill in the art configures and trains a neural network in step 202, as discussed in some detail in the brief overview of neural networks above. Upon completion of the training process, and based on the historical database of patient information, nominal values for each input field are determined in step 204. Finally, in step 206, the network parameters, structural information, weight coefficients of neural network 20 corresponding to the given medical condition, as well as the nominal input values characteristic for the condition are stored for later use.

Referring back to FIG. 3, it illustrates the process of producing and storing a diagnostic score from a patient's data record. Specifically, the parameters of the trained neural network and its nominal input values are retrieved from the storage 16 in step 302. The current patient's data record is retrieved from the user interface at step 304. As shown in FIG. 10, this can be accomplished by entering the information on the keyboard 14 or, more typically, by reading a data record that can be stored in memory 16 or communicated remotely via interface 22.

Along one path of the divergent order pointer 312, the current data record is passed to the trained neural network 20 for further processing. In step 306 the trained neural network 20 processes the data record to yield a diagnostic score which is generally indicative of the likelihood of the medical condition. This score is stored for later use in step 308. With reference to FIG. 10, the computed diagnostic score 316 is stored in memory 16, and can be displayed concurrently on display 18 to assist the physician.

Interpretation of the Diagnostic Score

FIG. 4 is a high level block diagram illustrating the interpretation of the diagnostic score produced by the neural network in accordance with the present invention. Specifically, proceeding along the path of the divergent order pointer 312, the current patient's data record is processed by the interpreter unit 25 in explanation step 402. In accordance with a preferred embodiment of the present invention this process yields a contribution list containing estimates of the contributions of the input factors that make up the diagnostic score 316. In step 404 the contribution list is sorted in descending order by magnitude such that larger contributions, positive or negative, to the diagnostic score appear earlier in the list. Sorting routines that can be used in step 404 are well known in the art and will not be discussed in further detail. At step 406, interpreter 25 stores the sorted list of factors for further use. In a preferred embodiment of the present invention, the sorted list is also displayed on display 18 in an appropriate format to assist the medical practitioner in providing a diagnosis.

The operation of interpreter 25 performing explanation step 402 is described in greater detail with reference to FIGS. 6, 7, 8, 9A and 9B. More specifically, these figures illustrate the process of providing a catalogue or a list of contributions of input factors, which comprises nominal contributions, individual contributions, pair contributions, triplet contributions, and others, as defined and described in more detail next.

Conceptually, the operation of interpreter unit 25 is separated into four submodules 402 (A–D) that perform different complementary functions as part of explanation step 402. More or less submodules can be used in alternate embodiments of the system 10. In accordance with a preferred embodiment of the present invention submodules 402 (A–D) of interpreter unit 25 can be implemented separately, or share common routines. Dependent on the preferred implementation, two or more output values provided by the submodules can be computed in parallel or sequentially. Following is a more detailed description of the operation of each submodule.

Figure 6:
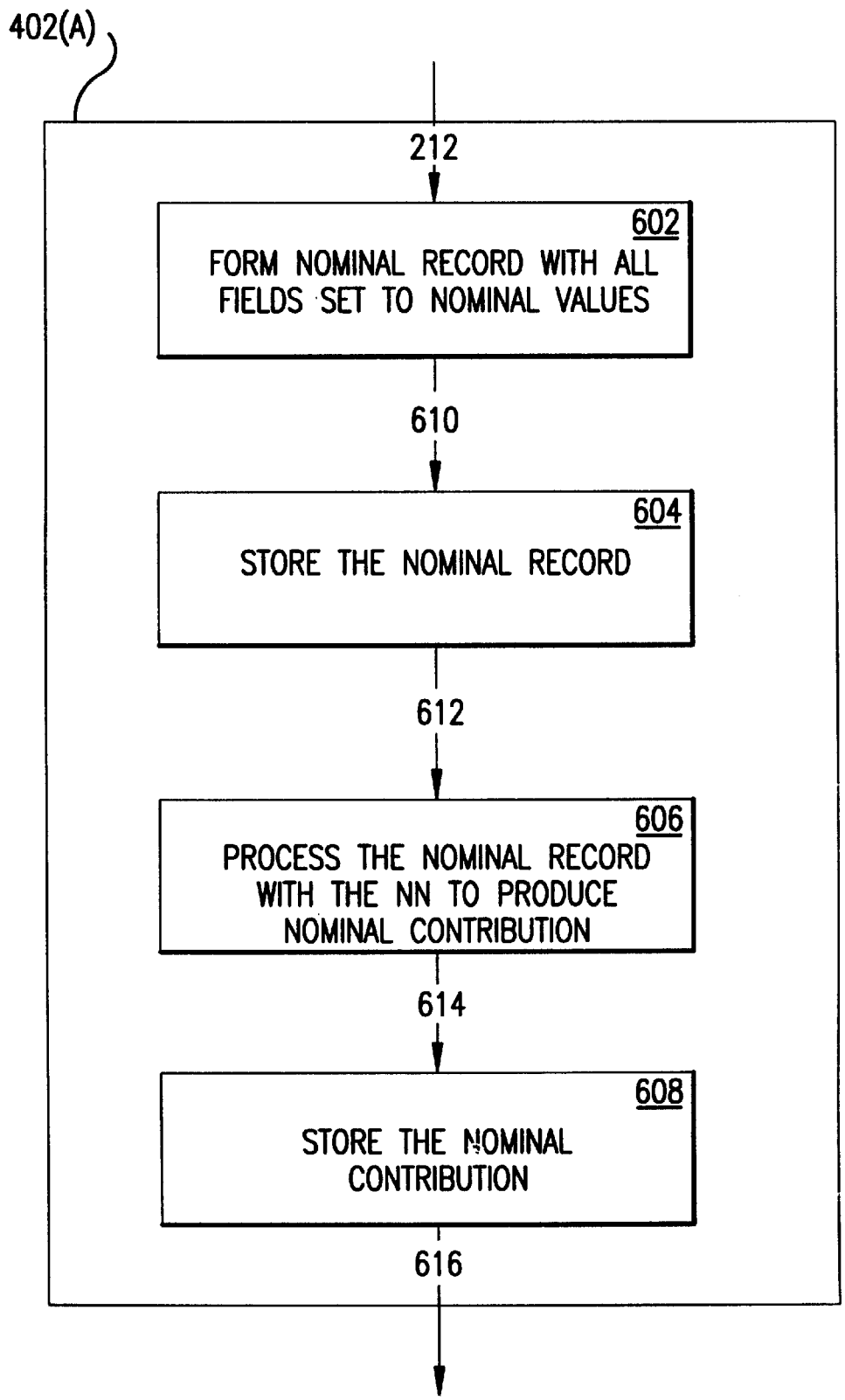
FIG. 6 illustrates the determination of a nominal contribution to the diagnosis score produced by the neural network in accordance with the present invention.

FIG. 6 illustrates the computation of the nominal contributions of input factors characteristic for a given medical condition. The corresponding submodule of interpreter 25 is labeled 402(A). As shown in the figure, in the first step of the operation of submodule 402(A), the network parameters and nominal input values 212 of a neural network trained to recognize given medical conditions are retrieved. From the nominal input values, in step 602 interpreter unit 25 constructs the nominal input record having all fields set to the nominal input values. In step 604 the nominal record is stored for later use. In step 606 the trained neural network 20, or a separately implemented copy of it, processes the nominal record and the diagnostic score corresponding to the nominal record. This score is referred to in the sequel as the nominal contribution. In step 608, the nominal contribution is stored for later use.

Figure 7:
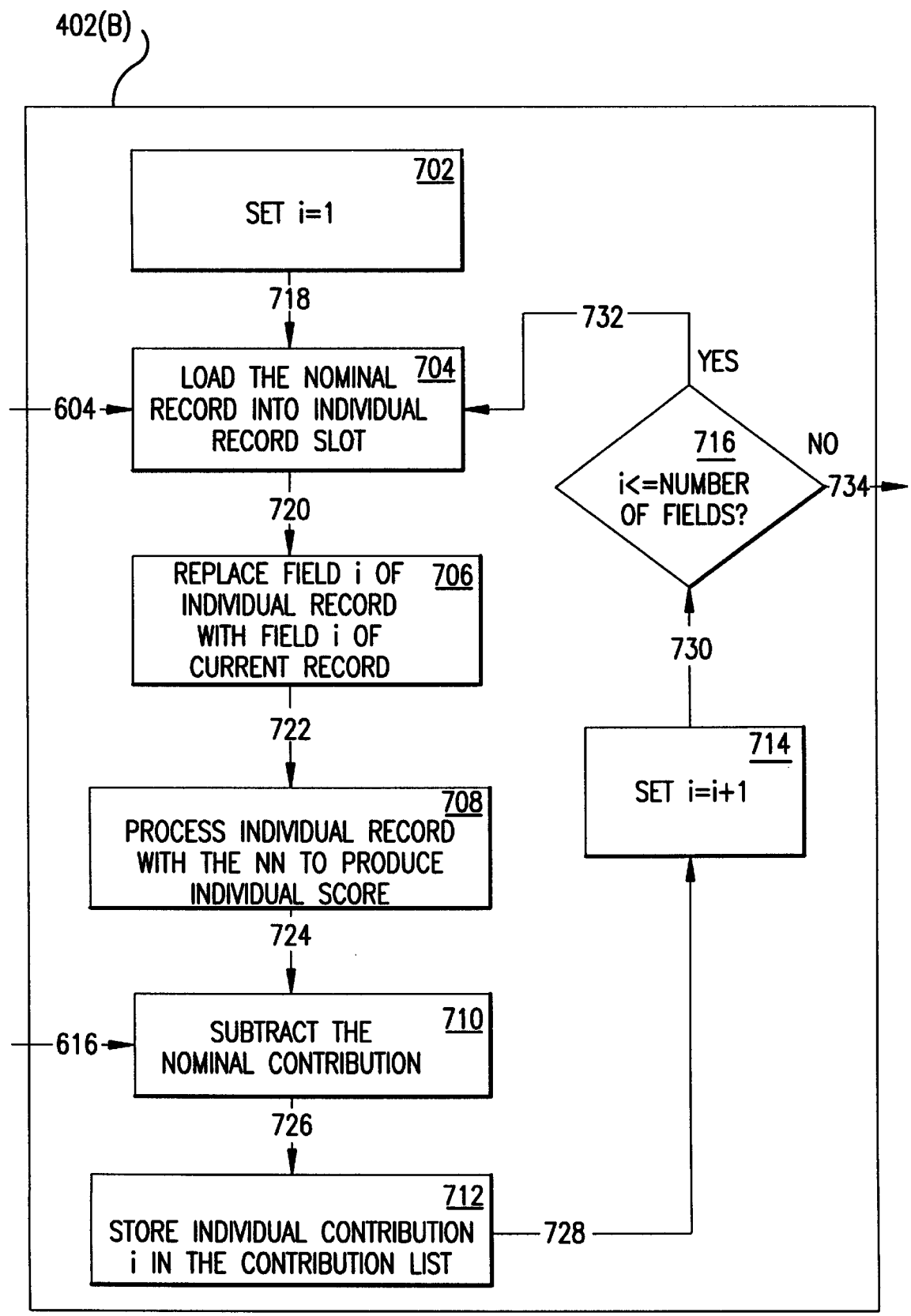
FIG. 7 illustrates the computation of the individual contributions to the diagnosis score in accordance with a preferred embodiment of the present invention.

The second submodule of interpreter unit 25 of the present invention performs processing steps labeled 402(B) of the explanation step 402, as depicted in FIG. 7. In particular, this submodule is responsible for the collection of steps required to determine the individual contributions of input factors. The term individual contribution, as used in the present invention, refers to the effect of a single data field, acting alone, on the diagnostic score. An individual contribution is calculated for each field in the input patient record. The procedure used in a preferred embodiment of the present invention is described as follows.

In step 702, a field index i is set to 1, that is, to the first field. The contents of the individual record are filled with the contents of the stored nominal record 604 in step 704. To determine the effect of input field i acting alone, in step 706 the ith field of the individual record is replaced with the ith field of the current patient record. The constructed individual record is processed by the trained neural network in step 708 to produce the individual score. To obtain the individual contribution, in step 710 the stored nominal contribution 616 is subtracted from the individual score. The result, which is defined as the individual contribution, is stored in step 712 for later use. Proceeding along the return path 728 of the looping construct, the field index i is incremented by one in step 714. In the following step 716, the field index is compared to the number of fields in the input patient record. If the field index is less than or equal to the number of fields, control returns along the path 732 to step 704 to begin computation of the next individual contribution. If the field index is greater than the number of fields at step 716, the computation of all individual effects is complete, and control proceeds along path 734 to submodule 402(C) of the interpreter unit 25.

Figure 8:
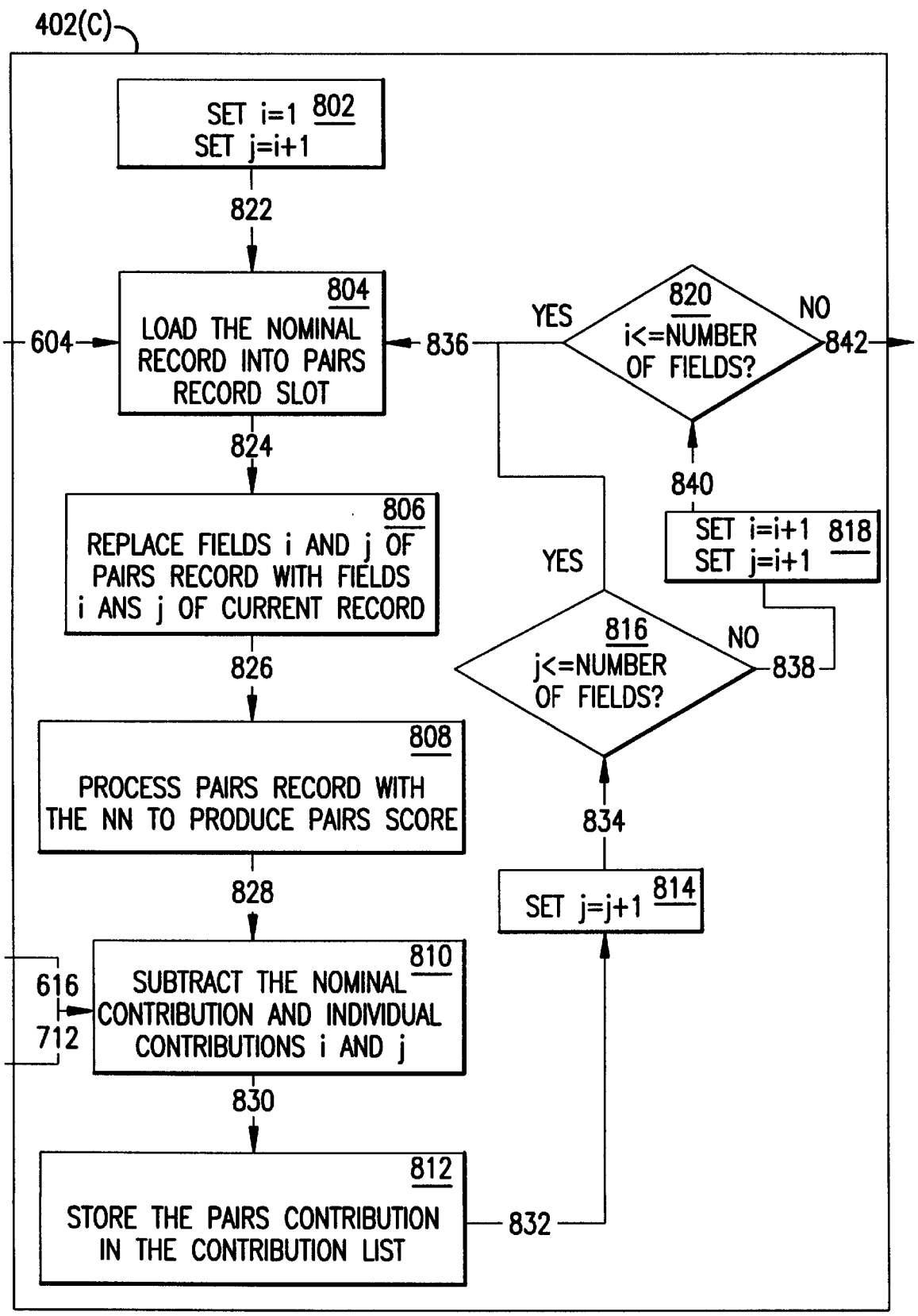
FIG. 8 shows the next step in the interpretation of a diagnosis score in accordance with the present invention which is the analysis of pairwise interactions.

Referring next to FIG. 8, submodule 402(C) of interpreter unit 25 determines and stores the contributions of pairwise interactions to the diagnostic score for the current patient's data record. The term pairwise interactions is used in the present invention to designate the effect of two input fields in the current data record acting together, independent of other effects. When control is passed to this submodule along path 734, in step 802 submodule 402(C) initializes two field indexes, i and j. Field index i is set to 1, and field index j is set to i+1. In step 804 of the operation, the pairs record is loaded with the stored nominal record 604. In a manner similar to that described for the individual record, fields i and j of the pairs record are replaced with fields i and j of the current data record in step 806. The trained neural network processes in step 808 the pairs record to produce a diagnostic score termed the pairs score. To obtain the pairs contribution for the pair i-j acting together, in step 810 the stored nominal contribution 616 and the stored ith and jth individual contributions 712 are subtracted. The pairs contribution result is stored in step 812 for later use.

Proceeding along the looping construct to step 814, field index j is incremented by one. At step 816, field index j is compared to the number of input fields in the data record. If field index j is less than or equal to the number of fields, control is passed back along path 836 to step 804 for computation of the next pair's contribution. If field index j is greater than the number of fields, control is passed along path 838 to step 818. In step 818, field index i is incremented by one, and field index j is reset to i+1. Field index i is then compared to the number of fields in step 820. If field index i is less than or equal to the number of fields, control is passed along path 836 to step 804 for the calculation of the next pairs contribution. Otherwise, the computation of all possible pairwise interactions is complete, and control is passed along path 842 to the triplet submodule 402(D) of the interpreter unit 25.

Figure 9A:
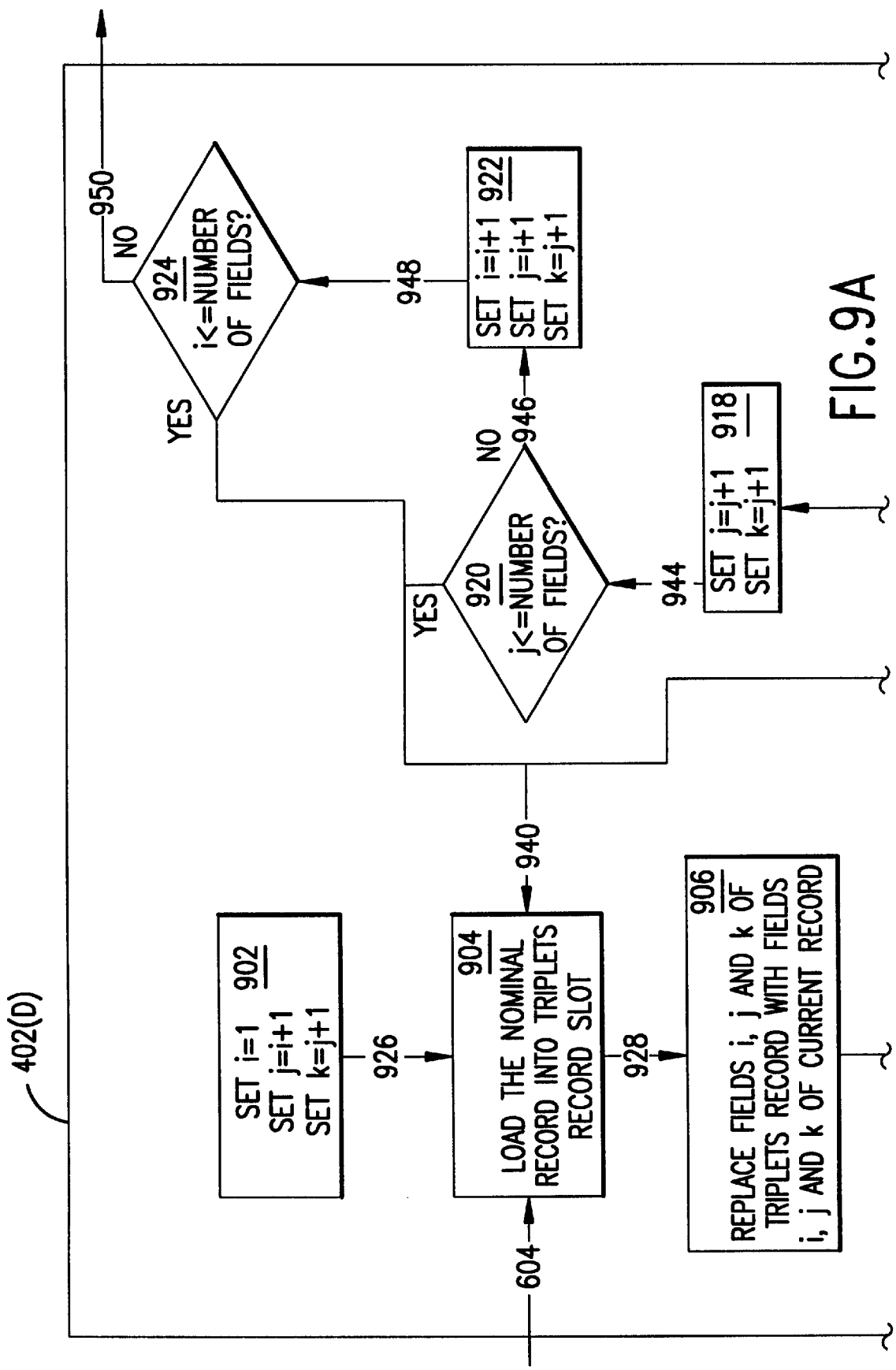
FIGS. 9A and 9B illustrate another step in the interpretation process in accordance with a preferred embodiment of the present invention which is the analysis of the three way interactions that contributed to the diagnosis score for the patient condition.
Figure 9B:
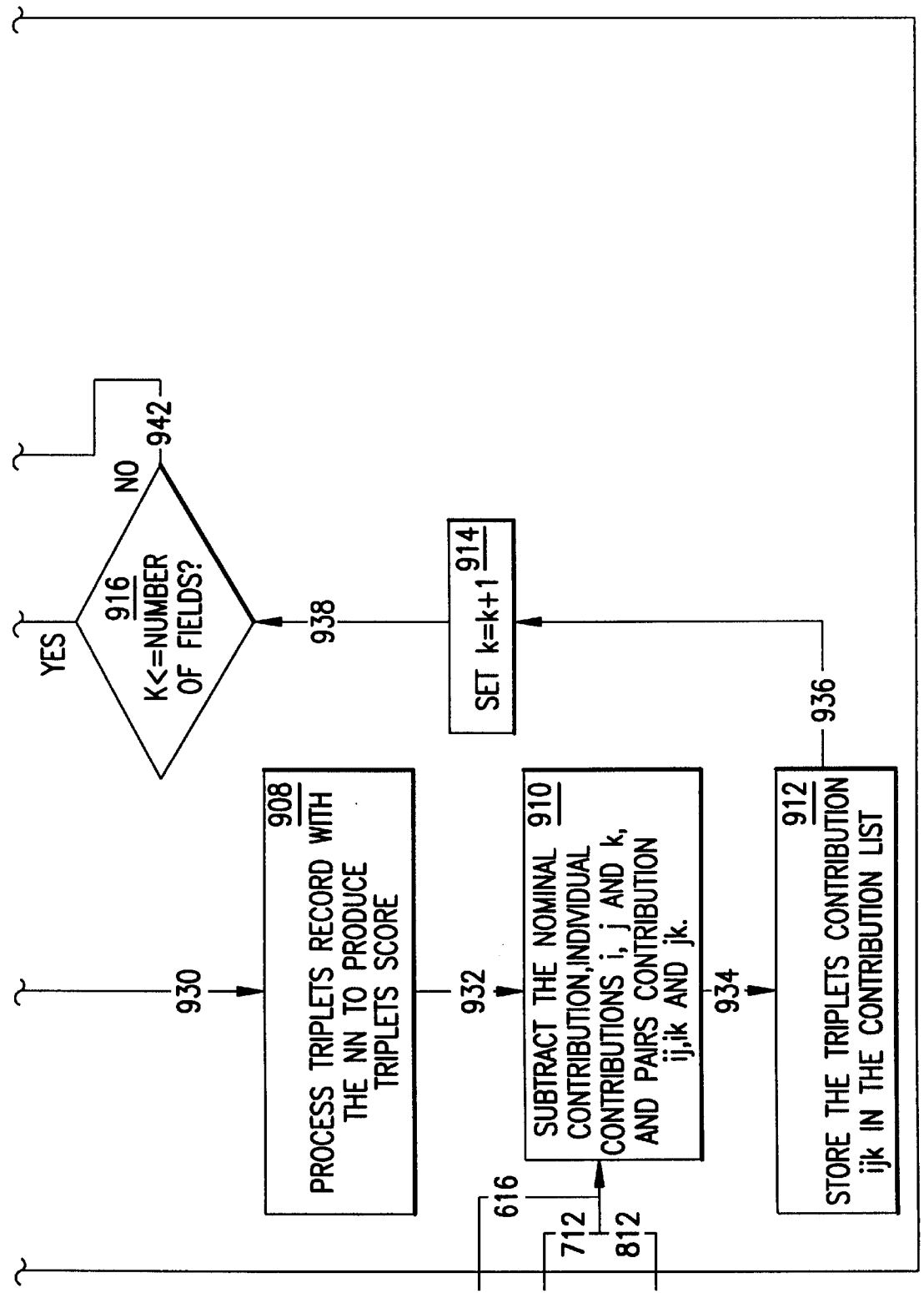

The operation of the last submodule 402(D) of interpreter unit 25 that performs the explanation step 402 in accordance with a preferred embodiment of the present invention is illustrated in FIGS. 9A and 9B. This submodule determines and stores the contributions of three-way interactions to the diagnostic score for the current data record. The term three-way interactions is used in this invention to refer to the effect of three input fields in the current data record acting together, independent of other effects. In particular, as shown in FIG. 9A control is passed along path 842 (see FIG. 8) to step 902 where three field indexes are initialized. Field index i is set to one, field index j is set to i+1, and field index k is set to j+1. In step 904, the stored nominal record 604 is retrieved and loaded into the triplets record. Proceeding to step 906, fields i, j, and k or the triplets record are replaced with fields i, j, and k of the current input record. As shown in FIG. 9B, the neural network 20 (or an identical copy of it) processes in step 908 the triplets record and produces a diagnostic score, referred to as the triplets score. To determine the triplets contribution from the triplets score, in step 910 the stored nominal contribution 616, the ith, jth, and kth individual contributions, and the i-jth, i-kth, and j-kth pairs contributions are subtracted. The resulting triplets contribution is stored in step 912 for later use.

Passing control along path 936 to step 914, field index k is incremented by one. At step 916, field index k is compared to the number of fields in the input record. If k is less than or equal to the number of fields, control is passed along path 940 to step 904 to begin computing the next triplets contribution. If k is greater than the number of fields, control is passed along path 942 to step 918 where field index j is incremented by one, and field index k is reset to j+1. Next, in step 920, field index j is compared to the number of input fields, If field index j is less than or equal to the number of fields, control is once again passed along path 940 to step 904. Otherwise, if field index j is greater than the number of fields, Control is passed along path 946 to step 922. In step 922, field index i is incremented by one. Field index j is set to i+1, and field index k is set to j+1. Proceeding to step 924, field index i is compared to the number of input fields. If field index i is less than or equal to the number of fields, control is passed a long path 940 to step 904. Otherwise, the computation of all three-way interaction s is complete, and control is passed along path 408 to step 404 for sorting of the contribution list, as described previously.

Output Display

Upon completion of the steps emanating from the divergent order pointer 312, the results of the input patient record processing are displayed on the display 18 for use by the physician. The stored diagnostic score 316 is retrieved and displayed first. Next, the stored, sorted contribution list 412 is retrieved and displayed in an appropriate format. At this point, the physician can review the results to aid in her or his diagnosis of the patient condition. The displayed results can be printed on printer 19 to create a record of the patient's condition. In addition with a specific preferred embodiment of the present invention the results can be communicated to other physicians or system users of computers connected to diagnostic system 10 via interface 22. The neural network system and method is then ready to score and interpret a new record, typically for a new patient.

User Interface

The diagnostic system 10 of the present invention, illustrated schematically in FIG. 10, utilizes a menu driven interface which allows the user to operate it easily. This approach makes the system of the present invention very user-friendly. In particular, it eliminates the need for the user to perform any computer programming in using the system, which is often a stumbling block in the application of software diagnostic systems.

Additionally, in a preferred embodiment the present invention provides real-time diagnostic system and method. Real-time operation demands, in general, that patient data be entered, processed, and displayed fast enough to provide immediate feedback to the physician in the clinical setting. In alternate embodiments, off-line data processing methods can be used as well. In a typical off-line operation, no attempt is made to respond immediately to the physician. The measurement and interview data in such case is generated some time in the past and stored for retrieval and processing by the physician at an appropriate time. It should be understood that the preferred embodiment of the present invention uses a real-time approach, alterative embodiments can substitute off-fine approaches in various steps.

Extensions and Applications

The diagnostic system and method of the present invention were described with reference to a specific application which is the use of the invention for the diagnosis of medical conditions. It should be clear, however, that the principles of this invention that provide for an enhanced interpretive facility that supplements a single score with an explanation and analysis of the relevant factors can also be used in a variety of different settings. For example, the present invention can readily be applied in areas as diverse as financial analysis, electronics design, oil exploration, and others. In particular, the interpretation of diagnostic scores provided by the present invention can be used in various complex systems for the purposes of prediction, planning, monitoring, debugging, repair and instruction. More specifically, results from the interpretation of systems scores obtained using neural networks can be used to develop production rules as part of an expert system, or to provide further insight into fuzzy relationships used in other artificial intelligence systems.

In addition, while the interpreter 25 of the present invention was discussed in the context of a particular system using four different submodules and computing the corresponding number of data interactions, it is clear that a modification and/or extension of the system to cover different practical situations should be straightforward, and should thus be considered to fall within the framework of the present invention. Further modifications of the system and method described in a preferred embodiment above can also be made in different applications.

The following example illustrates the use of the system and method of the present invention for the diagnosis of a particular medical condition.

EXAMPLE 1. Application to Breast Lesion Biopsy Diagnosis

The following example illustrates the application of the neural network 20 and interpreter 25 to the problem of ultrasound image interpretation for breast lesion biopsy diagnosis and recommendation. The experiment was conducted with a sample database of approximately 1000 images that were graded by physician experts. Statistical analyses and discussions with the physician experts yielded a set of 16 input features to be used for training the neural network. The single output was the recommendation, biopsy or no biopsy. Using conventional backpropagation training and cross validation procedures, a neural network with 8 hidden nodes was generated. Performance was evaluated as a combination of sensitivity and specificity. In particular, a sensitivity greater than 97% and a specificity greater than 60% was deemed acceptable for this application. Training was stopped when this level of performance was reached.

The neural network 20 and explanation functionality of interpreter 25 is encapsulated in a BIOPMODL program. The target platform for the application is the Silicon Graphics Indigo 2. In the implementation of the program, as portable a code was used as possible. Therefore the program is intended to compile in various machines without any specific modifications made to the code. All programs have been written in ANSI C.

Briefly, the BIOPMODL software package can be run in two modes, interactive and batch. In the interactive mode, the physician user is prompted for feature data via a text-based interface. In the batch mode, the user supplies a data file for processing. For each record that is entered manually or from a data file, the NeuralMed neural network engine produces a recommendation (biopsy or no biopsy), as well as an explanation of the major factors that contributed to the recommendation. In the interactive mode and the batch mode, these results are written to files. The application of the program is discussed in more detail below.

Interactive mode

A sample interactive session using the BIOPMODL program is shown below. The physician user simply enters the command biopmodl and the following prompted information exchange is begun. The physician is asked to fill in a series of feature values related to her or his assessment of an ultrasound image. More specifically, the following series was used:

Data in file, Y or N: n
Prefix name for report files: inter
Prompt for desired outcomes, Y or N: n
Convention for missing data is a value outside listed range MAMM2: mama mass 0=No, 1=Yes: 0

MAMM3: mamm asym density
0=No, 1=Yes: 0

SHAPE2: shape ovoid
0=No, 1=Yes: 0

SHAPE4: shape irreg
0=No, 1=Yes: 1

MARGIN1: margin linear
0=No, 1=Yes: 0

MARGIN2: margin poorly
0=No, 1=Yes: 1

ECHO3: echo hypo
0=No, 1=Yes: 1

ACUST1: acoustic edge
0=No, 1=Yes: 0

ACUST3: acoustic enhancement
0=No, 1=Yes: 0

PALBPLE: palpable
1=Yes, 2=No: 2

SIZEL: size long axis
0.01 to 5.10: 3.0

SIZEH: size height
0.01 to 4.10: 2.0

ORIENT: orientation to skin
1=Parallel, 2=Not Parallel: 2

DISTORT: distortion
0=no, 1 checked: 0

PVELOCTY: doppler peak velocity
0.30 to 70.30: 20.0

RI: resistive index
0.20 to 1.40: 0.5

Enter record 2, Y or N: n

When the physician user exits the data entry session, the result files inter.rpt and inter.sum are generated and stored. These result files are discussed in more detail in the Result Files section below.

Batch mode

A batch session of the package can be initiated in two different ways. In the first, by issuing the command biopmodl testfile the BIOPMODL package will read the data file named testfile.dat and produce the report and summary files testfile.rpt and testfile.sum, respectively.

Alternatively, a physician user can begin a batch session interactively as before by entering biopmodl A sample prompted interchange of this type is shown below.

Data in file, Y or N: y

Prefix name for dat (data) file and report files: testfile

Result Files

As mentioned earlier, the BIOPMODL package produces two types of result files. They are report (.rpt) files and summary (.sum) files. The contents of these files is described in detail below.

Report Files (.rpt)

The report (.rpt) files provide a recommendation for each data record that is provided, either manually entered or read from a file. Accompanying each recommendation is an explanation listing the major factors that contributed to the recommendation. These major factors are unique and critical features of the BIOPMODL package. They are particularly useful for gaining insight and understanding of the neural network recommendations. Following is an excerpt of a report file, along with a brief discussion of its components.

| BIOPMODL Results | |
| --- | --- |
| [1] = mamm mass | [9] = acoustic enhancement |
| [2] = mamm asym density | [10] = palpable |
| [3] = shape ovoid | [11] = size long axis |
| [4] = shape irreg | [12] = size height |
| [5] = margin linear | [13] = orientation to skin |
| [6] = margin poorly | [14] = distortion |
| [7] = echo hypo | [15] = doppler peak velocity |
| [8] = acoustic edge | [16] = resistive index |

15. Neural Network Result: Recommend Biopsy—Correct

| Major Contributions: | |
| --- | --- |
| Single [14] | (−) 15.8% |
| Triple [2] [5] [14] | (−) 15.4% |
| Triple [1] [2] [10] | (−) 14.8% |
| All Others | (+) 53.9% |

16. Neural Network Result: Recommend NO Biopsy—Correct

| Major Contributions: | |
| --- | --- |
| Triple [4] [5] [9] | (−) 22.4% |
| Triple [2] [5] [9] | (−) 19.4% |
| Triple [2] [4] [9] | (−) 19.0% |
| All Others | (+) 39.2% |

17. Neural Network Result: Recommend Biopsy—Correct

| 5 Major Contributions: | |
| --- | --- |
| Single [14] | (−) 15.6% |
| Triple [2] [5] [14] | (−) 15.2% |
| Triple [2] [4] [14] | (−) 14.3% |
| All Others | (+) 54.9% |

<. . . some results omitted for brevity. . . >

A numbered list of the data fields appears at the top of the file. This list is simply included for reference, particularly for identifying the major factors supplied in the explanation. For each record, beginning with record 15 in the excerpt above, the record number is printed, followed by the recommendation produced by the neural network. At the end of the line, if the true recommendation is known, the model recommendation is graded as being correct or incorrect.

(Note that the true recommendation is known only in program testing sessions where a set of previously evaluated results are being entered. In normal operation where a second opinion is sought, the correct recommendation is unknown.)

On the succeeding lines for each record, the top factors contributing to the recommendation are listed. The factors can be single factors, pair factors (the product of two features), and triple factors (the product of three features). For instance, the top contributors to the recommendation for record 15 are the single factor distortion ([14] in the list), the triple factor (mamm asym density)*(margin linear)*(distortion), and the triple factor (mamm mass)*(mamm asym density)*(palpable). These factors contribute 15.8%, 15.4%. and 14.8% to the overall recommendation. In parentheses, next to each factor is a (−) or (+) indicating whether that factor contributed in the direction of NO Biopsy or Biopsy, respectively. Notice that although the top three factors for record 15 all favor NO Biopsy, the sum of all the remaining factors (which sum to an amount greater than 50%, 53.9% in total) favors Biopsy, which is the correct recommendation. The situation is reversed in record 16 where once again, the major factors all favor NO Biopsy. However, in this case, they form a majority (over 50% compared to the 39.2% accounted for by all other factors) and support the network's recommendation of NO Biopsy.

Summary Files (.sum)

The summary (.sum) files provide a set of summary statistics for all data records processed in either an interactive or batch session. A summary file for the sample data follows, along with a discussion of its contents.

| BIOPMODL Summary Report | | | | | | | |
|---|---|---|---|---|---|---|---|
| Actual | | | Model | | | | |
| Tot | Neg | Pos | Corr Neg | False Pos | Corr Pos | False Neg | |
| 19 | 10 | 9 | 6 | 4 | 8 | 1 | |

Sensitivity = 88.9
Specificity = 60.0

The summary report is split into two major divisions: statistics for the actual (observed) recommendations and statistics for the model (predicted) recommendations. The subheadings under the actual division count the total number of records (Tot), the total number of negative NO Biopsy recommendations (Neg), and the total number of positive Biopsy recommendations (Pos). The subheadings beneath the model division count the number of correct negative recommendations (Corr Neg), the number of false positives (False Pos), the number of correct positive recommendations (Corr Pos), and the number of false negatives (False Neg). Finally, the bottom of the summary presents overall figures for sensitivity and specificity. Note that the results for this small sample are not indicative of the general accuracy. In fact, the measured sensitivity on a large sample was almost 97%, rivaling the accuracy of the physician experts.

Although the foregoing description and Example 1 refer to particular preferred embodiments, it will be understood that the present invention is not so limited. It will occur to those of ordinary skill in the art that various modifications can be made to the disclosed embodiments, and such modifications are intended to be within the scope of the present invention which is defined in the following claims.

We claim:

1. A method for diagnosis of a medical condition comprising the steps of:
   providing a plurality of input parameters representing characteristics of the medical condition;
   converting said plurality of input parameters into numerical data;
   inputting the numerical data to a neural network trained to detect the medical condition and determining a score indicative of the likelihood of the medical condition on the basis of the numerical data;
   interpreting the numerical data to provide estimates of the contribution of input parameters to the determined score; and
   displaying the determined score and the provided estimates in a human-readable form.

2. The method of claim 1 wherein said plurality of input parameters correspond to a single patient.

3. The method of claim 1 wherein the score determined by the neural network has values ranging between 0 and 1, with scores near 0 indicating low likelihood of the medical condition, and scores near 1 indicating high likelihood of the medical condition.

4. The method of claim 1 wherein the step of interpreting comprises analyzing at least a contribution to the determined score of each of the plurality of input parameters.

5. The method of claim 4 wherein the step of interpreting further comprises analyzing pairwise contributions to the determined score for each pair corresponding to different input parameters of said plurality of input parameters.

6. The method of claim 4 wherein the step of interpreting further comprises analyzing contributions to the determined score for at least each triplet corresponding to different input parameters of said plurality of input parameters.

7. The method of claim 1 wherein in the step of interpreting, the estimates of the contribution of input parameters are computed on the basis of nominal values for each of said plurality of input parameters representing characteristics of the medical condition.

8. The method of claim 1 wherein the step of displaying is substantially coincident with the step of providing a plurality of input parameters.

9. The method of claim 1 further comprising the step of providing a printed record of the determined score and the provided estimates.

10. The method of claim 1 further comprising the step of communicating the determined score and the provided estimates to a remote location.

11. A system for diagnosis and interpretation of a medical condition comprising:
    means for providing a plurality of input parameters representing characteristics of the medical condition, the plurality of input parameters being provided as numerical data;
    a neural network trained to detect the medical condition for determining a score indicative of the likelihood of the medical condition on the basis of the numerical data;
    means for interpreting the numerical data to provide estimates of the contribution of input parameters to the determined score; and
    display means for displaying the determined score and the provided estimates in a human-readable form.

12. The system of claim 11 wherein said means for providing comprises input means for entering data and storing such data into a data storage.

13. The system of claim 11 wherein the score determined by the neural network has values ranging between 0 and 1, with scores near 0 indicating low likelihood of the medical condition, and scores near 1 indicating high likelihood of the medical condition.

14. The system of claim 11 wherein the means for interpreting comprises first data processing means for analyzing at least a contribution to the determined score of each of the plurality of input parameters.

15. The system of claim 14 wherein the means for interpreting further comprises a second data processing means for analyzing contributions to the determined score for at least each data pair corresponding to different input parameters of said plurality of input parameters.

16. The system of claim 15 wherein the means for interpreting further comprises means for computing nominal values for each of said plurality of input parameters representing characteristics of the medical condition.

17. The system of claim 16 wherein the first data processing means, the second data processing means and the means for computing nominal values process the numerical data in parallel.

18. The system of claim 11 wherein the means for displaying comprises a computer monitor.

19. The system of claim 11 further comprising a printer for providing a printed record of the determined score and the provided estimates.

20. The system of claim 11 further comprising means for communicating the determined score and the provided estimates to a remote location.

21. A computer-based system to assist the diagnosis of a medical condition, comprising:

a patient record comprising numerical data representing a plurality of input factors associated with characteristics of the medical condition;

a neural network responsive to said patient record and configured to determine a score indicative of the likelihood of the medical condition in the patient record;

a computer interpreter responsive to said patient record for estimating the contribution of said plurality of input factors to the score determined in the neural network; and a display for displaying the determined score and the estimates provided by the interpreter in a human-readable form to assist the diagnosis of the medical condition.

22. The system of claim 21 further comprising data storage for storing one or more patient records.

23. The system of claim 21 wherein the interpreter comprises first data processing means for analyzing at least a contribution to the determined score of each of said plurality of input parameters.

24. The system of claim 23 wherein the interpreter further comprises a second data processing means for analyzing contributions to the determined score for at least each data pair corresponding to different input parameters of said plurality of input parameters.

25. The system of claim 24 wherein the interpreter further comprises means for computing nominal values for each of said plurality of input parameters on the basis of training the neural network with patient records bearing known association with the medical condition.

26. The system of claim 21 further comprising a printer for providing a printed record of the determined score and the provided estimates.

27. The system of claim 21 further comprising interface means for communicating data to a remote location.

28. The system of claim 27 wherein said interface means is a modem.

29. The system of claim 27 wherein the communication of data to said remote connection is accomplished over packet switched networks, such as the Internet.

* * * * *